United States Patent
Cunningham et al.

(10) Patent No.: US 7,171,844 B2
(45) Date of Patent: Feb. 6, 2007

(54) APPARATUS AND METHOD FOR MEASURING THE MASS OF A SUBSTANCE

(75) Inventors: Brian T. Cunningham, Lexington, MA (US); John R. Williams, Lexington, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 11/352,610

(22) Filed: Feb. 13, 2006

(65) Prior Publication Data

US 2006/0123910 A1 Jun. 15, 2006

Related U.S. Application Data

(62) Division of application No. 09/543,612, filed on Apr. 5, 2000, now abandoned.

(51) Int. Cl.
*G01N 5/04* (2006.01)
*G01N 25/08* (2006.01)

(52) U.S. Cl. ............... 73/73; 73/580; 73/61.75; 374/27

(58) Field of Classification Search ............ 73/61.45, 73/61.49, 61.75, 61.79, 64.53, 73, 76, 579, 73/580, 865; 374/27
See application file for complete search history.

(56) References Cited

U.S. PATENT DOCUMENTS

| 3,561,253 | A |   | 2/1971  | Dorman              |
|-----------|---|---|---------|---------------------|
| 4,566,312 | A | * | 1/1986  | Collins et al. ...... 73/32 A |
| 4,596,697 | A | * | 6/1986  | Ballato ............... 422/98 |
| 4,685,326 | A | * | 8/1987  | Peterson ............. 73/38 |
| 4,827,760 | A |   | 5/1989  | Saito               |
| 5,006,749 | A |   | 4/1991  | White               |
| 5,072,427 | A |   | 12/1991 | Knowles             |
| 5,129,262 | A | * | 7/1992  | White et al. ......... 73/599 |
| 5,177,327 | A |   | 1/1993  | Knowles             |
| 5,189,914 | A |   | 3/1993  | White et al.        |
| 5,212,988 | A | * | 5/1993  | White et al. ......... 73/599 |
| 5,299,175 | A |   | 3/1994  | Gallego-Juarez et al. |
| 5,412,207 | A |   | 5/1995  | Micco et al.        |
| 5,450,752 | A |   | 9/1995  | White et al.        |
| 5,476,002 | A |   | 12/1995 | Bowers et al.       |

(Continued)

FOREIGN PATENT DOCUMENTS

EP      0 215 669 A2     3/1987

(Continued)

OTHER PUBLICATIONS

Brian Stark, "Common Device Elements" in *MEMS Reliability Assurance Guidelines for Space Applications*, Chapter 6, JPL Publication 99-1, Jan. 1999, pp. 91-151.

*Primary Examiner*—John E. Chapman
(74) *Attorney, Agent, or Firm*—Iandiorio & Teska

(57) ABSTRACT

An apparatus for measuring the mass of a substance includes a sensor having a membrane layer, the membrane for receiving the substance thereon, an oscillator device for driving the membrane at a reference resonant frequency, a frequency detection device for determining a change in the reference resonant frequency caused by the presence of the substance on the membrane, and a mass determining device for determining the mass of the substance, the change in the reference resonant frequency being indicative of the mass of the substance.

15 Claims, 12 Drawing Sheets

U.S. PATENT DOCUMENTS

| | | |
|---|---|---|
| 5,571,944 A | 11/1996 | Pfeifer et al. |
| 5,591,914 A | 1/1997 | White et al. |
| 5,652,672 A | 7/1997 | Huignard et al. |
| 5,661,233 A | 8/1997 | Spates et al. |
| 5,679,906 A | 10/1997 | Van Cleve et al. |
| 5,836,203 A | 11/1998 | Martin et al. |
| 5,918,258 A * | 6/1999 | Bowers .................. 73/24.06 |
| 6,106,149 A * | 8/2000 | Smith ..................... 374/31 |
| 6,286,370 B1 | 9/2001 | Sinha |
| 6,386,053 B1 | 5/2002 | Takeuchi et al. |

FOREIGN PATENT DOCUMENTS

| | | |
|---|---|---|
| EP | 0 779 510 A2 | 6/1997 |
| JP | 63214653 A | 9/1988 |
| JP | 02090050 A | 3/1990 |
| JP | 02118434 A | 5/1990 |
| JP | 02261137 A | 10/1990 |
| JP | 06194290 A | 7/1994 |
| JP | 07209164 A | 8/1995 |
| JP | 10307095 A | 11/1998 |
| JP | 11352045 A | 12/1999 |
| WO | WO 98/40739 A1 | 9/1998 |
| WO | WO 99/28735 A1 | 6/1999 |

\* cited by examiner

APPARATUS AND METHOD FOR MEASURING THE MASS OF A SUBSTANCE

RELATED APPLICATIONS

This application is a divisional application of U.S. patent application Ser. No. 09/543,612, filed on Apr. 5, 2000, now abandoned incorporated herein by reference.

FIELD OF INVENTION

This invention relates generally to an apparatus and method for measuring the mass of a substance, and more particularly to an apparatus and method for monitoring the reference resonant frequency of a flexural plate wave sensor, determining the change in frequency after the substance is placed on the sensor and the determining the mass of the substance based on the change in the reference resonant frequency.

BACKGROUND OF INVENTION

Prior art mass measuring devices, such as microbalances, are capable of measuring substances within the microgram range. However, in some circumstances, it is necessary to measure the mass of a substance or the change in the mass of a substance which is in the nanogram or subnanogram range. Such circumstances include the determination of the moisture content of a substance, the boiling point of a substance and the determination of a concentration of non-volatile residues (NVR) in solvents.

One prior art method for determining the concentration of a NVR in a solvent involves boiling a large quantity of a solvent sample, typically a liter or more, in a glass container until the entire sample is evaporated. Any material remaining after the boiling process is non-volatile residue. A microbalance is then used to measure the weight of the material remaining after boiling. However, this process has many disadvantages. First, a large quantity of solvent must be boiled away in order to provide enough mass gain to be resolved by the microbalance; boiling and measuring operation can take several hours; and the boiled solvent is exhausted into the atmosphere. The procedure is labor intensive and reproducibility problems are present due to the ease of contamination during long exposure time of the sample to the atmosphere during the boiling process.

SUMMARY OF THE INVENTION

It is therefore an object of the present invention to provide a method and apparatus for determining the mass of a substance.

It is a further object of the invention to provide such an apparatus and method that is capable of determining the mass of a substance with a resolution in the nanogram or subnanogram range.

It is further object of the invention to provide such a method and apparatus that is capable of determining the mass of a substance in a quick and simple manner.

It is a further object of the invention to provide such as apparatus and method that monitors the change in the reference resonant frequency of a flexural plate wave sensor to determine the mass of a substance disposed on the sensor.

It is a further object of the invention to provide such a method and apparatus for determining the concentration of the substance in a solution, based on the determination of the mass of the substance.

It is a further object of the invention to provide such a method and apparatus for determining the moisture content of the substance based on the determination of the mass of the substance.

It is yet a further object of the invention to provide such a method and apparatus for determining the boiling point of the substance based on the reduction in the mass of the substance as the substance is heated.

The invention results from the realization that a truly effective mass determining device can be obtained by driving the membrane of a flexural plate wave sensor at a reference resonant frequency, placing a substance on the membrane of the flexural plate wave sensor, determining the frequency change in the membrane as the result of the deposition of the substance on the membrane and determining the mass of the substance based on the change in the frequency within the membrane. The concentration of a substance within a solution can be determined by comparing the mass of the substance, which is determined based on the frequency change within the membrane, to the volume of the solution in which the substance is located. The moisture content of the substance also can be determined by determining the mass of the substance based on the frequency change within the membrane, heating the substance to evaporate moisture contained within the substance and determining the mass of the substance after the moisture is driven off, wherein the change in the mass of the substance is a result of the heating process is indicative of the moisture content of the substance. Furthermore, the boiling point of a substance also can be determined based on the rate of the change of the mass of the substance as it is heated.

This invention features an apparatus for measuring the mass of a substance including a sensor having a membrane layer, the membrane for receiving the substance thereon, an oscillator device for driving the membrane at a reference resonant frequency, a frequency detection device for determining a change in the reference resonant frequency caused by the presence of the substance on the membrane and a mass determining device for determining the mass of the substance, the change in the reference resonant frequency being indicative of the mass of the substance.

In a preferred embodiment, the sensor maybe a flexural plate wave sensor. The flexural plate wave sensor may be formed from a silicon substrate and the membrane may be formed from a silicon layer. The flexural plate wave sensor may further include a piezoelectric layer formed on the membrane, a first transducer disposed on the piezoelectric layer and a second transducer disposed on the piezoelectric layer, spaced from the first transducer. The oscillator device may be connected to the first transducer for driving the membrane at the reference frequency and the frequency detection device may be connected to the second transducer for determining the change in the reference resonant frequency. The sensor may further include a plurality of walls peripheral to the membrane, the plurality of walls cooperating to define a cavity having the membrane as a bottom portion thereof. The deposition of the substance on the membrane may cause a decrease in the reference resonant frequency, thereby indicating an increase in the mass disposed on the membrane. An increase in the reference resonant frequency may indicate a decrease in the mass of the substance on the membrane. The substance may be present in a volume of a volatile solution which is deposited on the membrane, the mass of the substance being measured after the solution evaporates, leaving the substance on the membrane. The apparatus may further include a concentration determining device for comparing the mass of the substance to the volume of the solution to determine the concentration of the substance within the volume of the solution. The substance may be a non-volatile residue. The apparatus may further include a display device connected to the microprocessor for displaying the mass of the substance. The apparatus may further include a heating device for heating the substance after it has been deposited on the membrane to evaporate moisture from the substance, the frequency detection device determining the change in the reference frequency after the moisture is evaporated from the substance. The apparatus may further include a moisture content determining device, wherein the mass determining device determines the mass of the substance after the substance is heated and the moisture content determining device determines the moisture content of the substance by comparing the mass of the substance before it is heated to the mass of the substance after it is heated. The apparatus may further include a boiling point determining device, wherein the heating device may heat the substance with a temperature which is increasing at a constant rate which causes the reference resonant frequency to increase at a first rate as the mass of the substance decreases, the frequency detection device may monitor the rate of change of the reference resonant frequency as the substance is heated and the boiling point determining device may determine the boiling point of the substance as the temperature when the rate of change of the reference frequency becomes greater than the first rate. The apparatus may include a plurality of sensors configured in an array, each of the sensors being connected between the oscillator device and the frequency detection device.

The invention also features a method for measuring the mass of a substance, including the steps of driving a membrane of a sensor at a reference resonant frequency, depositing the substance onto the membrane of the sensor, measuring a shifted frequency within the membrane, detecting a change of the shifted frequency from the reference frequency, and determining the mass of the substance based on the change of the shifted frequency from the reference resonant frequency.

In a preferred embodiment, the depositing step may include placing a volume of volatile solution containing the substance on the membrane and allowing the solution to evaporate, the substance thereby remaining on the membrane. The method may further include the step of comparing the mass of the substance to the volume of the solution to obtain the concentration of the substance within the solution. The method may further may further include the steps of heating the substance after the mass of the substance is determined to drive out any moisture in the substance, measuring the post-heating frequency in the membrane after the heating step, detecting a change of the post-heating frequency from the shifted frequency, and determining the mass of the substance after the heating step based on the change of the post heating frequency from the shifted frequency. The method may further include the step of determining the moisture content of the substance before the heating step takes place, based on the difference in the mass of the substance before the heating step and the mass of the substance after the heating step. The depositing step may include placing the sensor in a fluid environment and allowing a volatile solution contained in the fluid environment to collect on the membrane.

The invention also features an apparatus for measuring a change in the mass of a substance within the subnanogram range.

BRIEF DESCRIPTION OF THE DRAWINGS

Other objects, features and advantages will occur to those skilled in the art from the following description of a preferred embodiment and the accompanying drawings, in which.

PREFERRED EMBODIMENT

Figure 1:
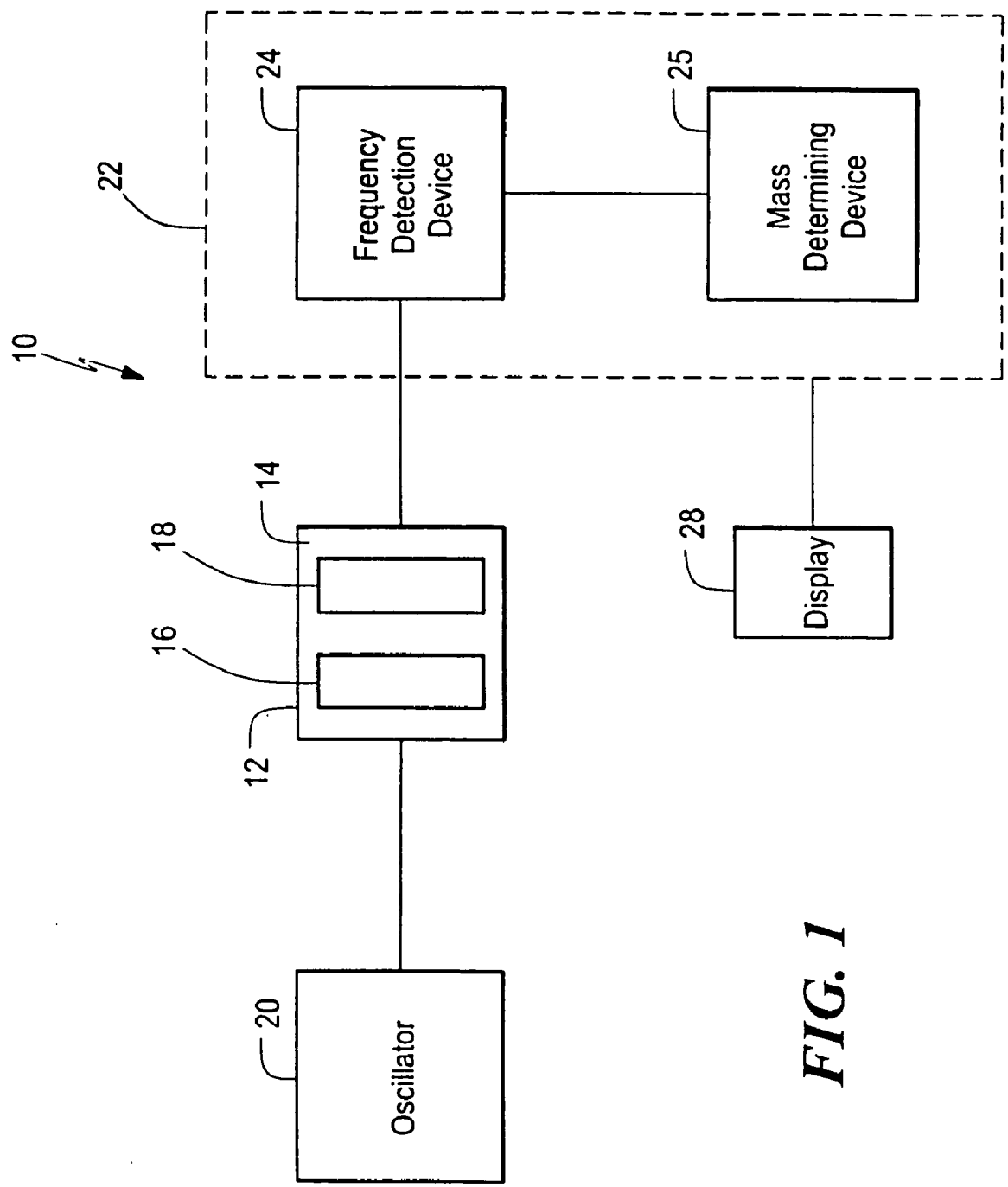
FIG. 1 is a block diagram of the mass determining apparatus in accordance with the present invention.

Mass measuring system 10, shown schematically in FIG. 1, includes a flexural plate wave sensor 12 including a membrane 14, a first transducer 16 and a second transducer 18, both disposed on membrane 14. An oscillator 20 is connected to transducer 16 for driving the membrane at a reference resonant frequency. Transducer 18 receives this frequency and transmits it to a microprocessor 22 which includes a frequency detection device 24 and a mass determining device 26. An optional display 28 may be connected to the microprocessor 22 for displaying the values determined by the system 10.

Figure 2:
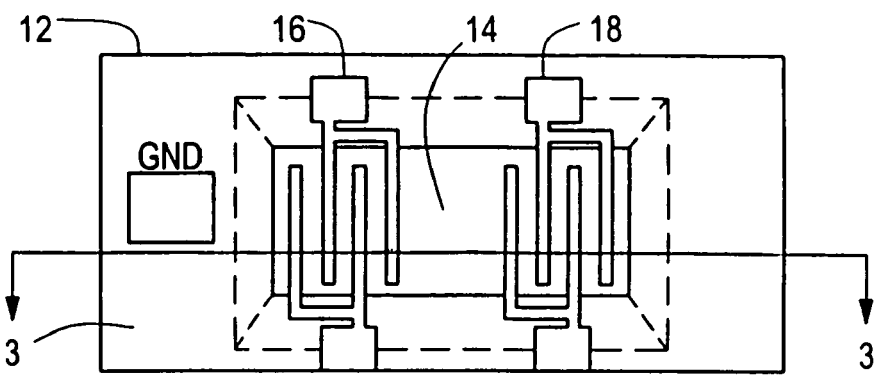
FIG. 2 is a bottom view of the flexural plate wave sensor in accordance with the present invention.
Figure 3:
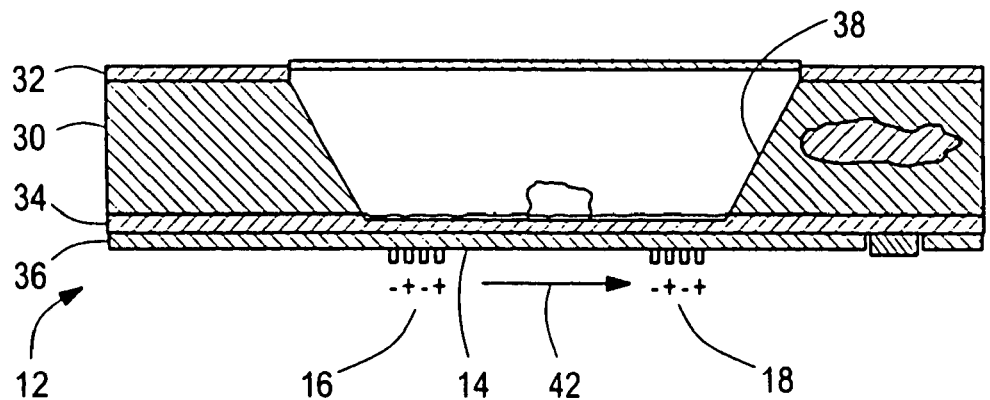
FIG. 3 is cross sectional side view of the flexural plate wave sensor in accordance with the present invention, taken along line 3—3 of FIG. 2.

As shown in FIGS. 2 and 3, sensor 12 includes a structural layer 30 which is preferably formed from undoped silicon, a lower layer 34 which is preferably formed from boron-doped silicon and a piezoelectric layer 36 which is preferably formed from a piezoelectric material such as aluminum nitride. Sensor 12 includes a cavity 38 (shown in phantom in FIG. 2) which is etched into the upper layer 32 and structural layer 30, leaving lower layer 34 exposed within the cavity. The exposed portion of lower layer 34 forms the membrane 14 of the sensor 12. Transducers 16 and 18 are preferably interdigitated transducers.

In operation, oscillator 20 causes transducer 16 to transmit a wave at a reference frequency in the direction of arrow 42 which wave is received by transducer 18. The wave received by transducer 18 it is transmitted to frequency detection device 24 of microprocessor 22. Generally, as long as the mass per unit area of the membrane 14 does not change, the reference frequency input by transducer 16 and received by transducer 18 remains constant. However, when the mass per unit area of the membrane increases or decreases, such as when a substance is deposited or removed from the membrane, a frequency shift in the wave received by the transducer 18 results.

Figure 4:
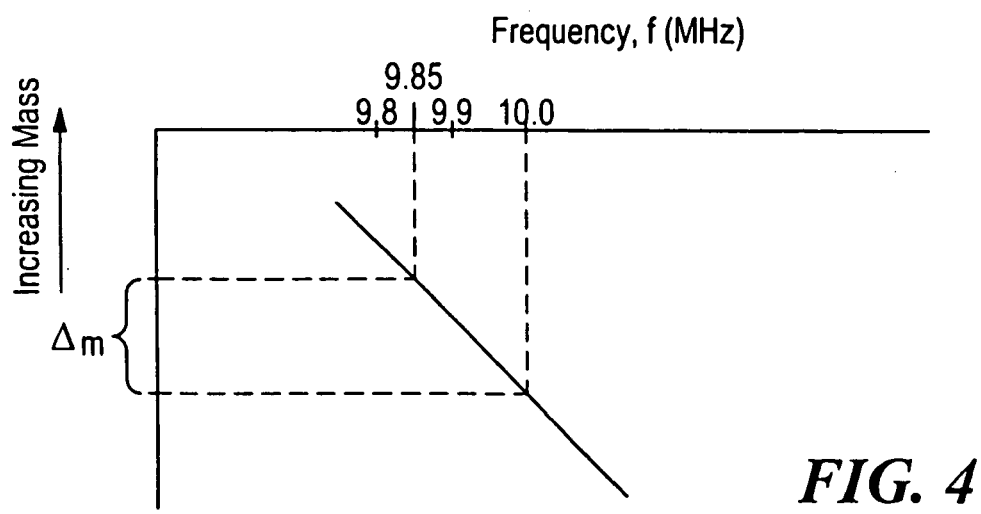
FIG. 4 is a graph which shows the effect on the frequency within the membrane of the sensor of the present invention to an increase in the mass of the membrane in accordance with the present invention.
Figure 5:
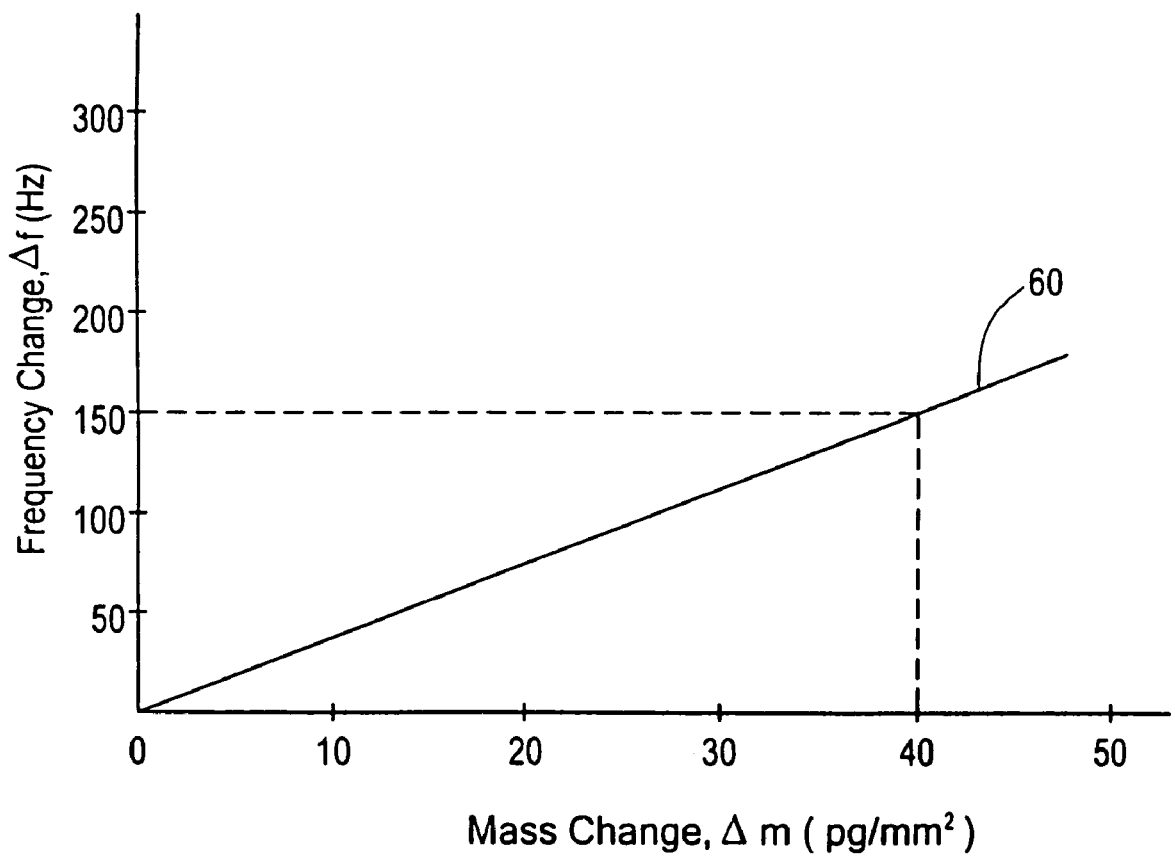
FIG. 5 is a graph which shows the effect of the mass of a substance on the membrane of the sensor of the present invention on the frequency present within the membrane in accordance with the present invention.

The amount of the change in the frequency within the membrane 14 is inversely proportional to the change in the mass on the membrane 14. For example, as shown in FIG. 4, if the mass of the membrane 14 is at a steady state and the reference frequency is 10 MHz, an increase in the mass of the membrane by an amount Δm causes the frequency in the membrane to decrease to 9.85 MHz. By knowing that the frequency of the membrane has decreased by 150 Hz, the change in the mass of the membrane can be determined. The relationship between the mass change Δm and the frequency change Δf is shown in the graph of FIG. 5. The mass sensitivity, $S_m$, of the sensor 12, which defines the relationship between the mass and frequency changes, is determined using the following equation:

$$S_m = \frac{(\Delta f / f_{ref})}{(\Delta m / A)}, \quad (1)$$

where $f_{ref}$ is the reference resonant frequency input to the membrane through transducer 16 and A is the area of the membrane, which in the preferred embodiment is 5.0 mm². Accordingly, the mass sensitivity $S_m$ is determined by driving the membrane 14 at a reference resonant frequency, placing a substance of a known mass, Δm, on the membrane and measuring the change Δf in the reference resonant frequency. The relationship between changes in the mass of the membrane Δm and the resulting changes in the frequency within the membrane Δf is then plotted to obtain the line 60.

Once the mass sensitivity $S_m$ is known for the particular sensor 12, the mass of a substance placed on the membrane 14 can be determined with the following equation:

$$\Delta m = \frac{\Delta f}{f} \cdot \frac{A}{S_m} \quad (2)$$

Referring to the above example, if the reference frequency $f_{ref}$ input to the membrane 14 by oscillator 20 through transducer 16 is 10 MHz and the deposition of a substance of an unknown mass Δm causes the frequency, $f_{ref}$, within the membrane 14 to shift to 9.85 MHz, representing a frequency change, Δf, of 150 Hz. Using Equation (2), it can be determined that this frequency change Δf corresponds to a mass change Δm of 2×10⁻¹⁰ g/mm², as shown in FIG. 5.

The operation of the system 10 will now be described with reference to FIG. 6. First, oscillator 20 generates a wave of a reference frequency $f_{ref}$ which is input to transducer 16 to drive the sensor membrane 14 at this reference frequency $f_{ref}$, step 62. A substance is then deposited on the membrane 14, step 64, which causes a shift in the reference frequency. This shifted frequency, $f_s$, is received by transducer 18 and input to frequency detection device 24 which measures the shifted frequency $f_s$, step 66. Frequency detection device 24 then detects the frequency change in the membrane between the shifted frequency and the reference frequency by subtracting the shifted frequency from the reference frequency ($\Delta f = f_{ref} - f_s$), step 68 and outputs the frequency change, Δf, to mass determining device 26 which determines the mass of the substance based on the change in the frequency Δf, step 70.

Accordingly, as oscillator 20, FIG. 1, drives the membrane 14 at the reference resonant frequency $f_{ref}$ of 10 MHz through the transducer 16, frequency detection device 24 of microprocessor 22 receives the frequency f detected by transducer 18. When a substance of unknown mass Δm is placed on the membrane 14, causing shifted frequency, $f_s$ of 9.85 MHz to be received by transducer 18, the shifted frequency $f_s$ is input into frequency detection device 24. Frequency detection device 24 determines the change in frequency, Δf, which is 150 Hz. This value is input to mass determining device 26 which uses Equation (2), which is shown graphically in FIG. 5, to determine the mass of the substance on the membrane 14 which, as discussed above, is 40 picograms/mm². Optional display 28 may then be used to display the resulting mass value.

Figure 6:
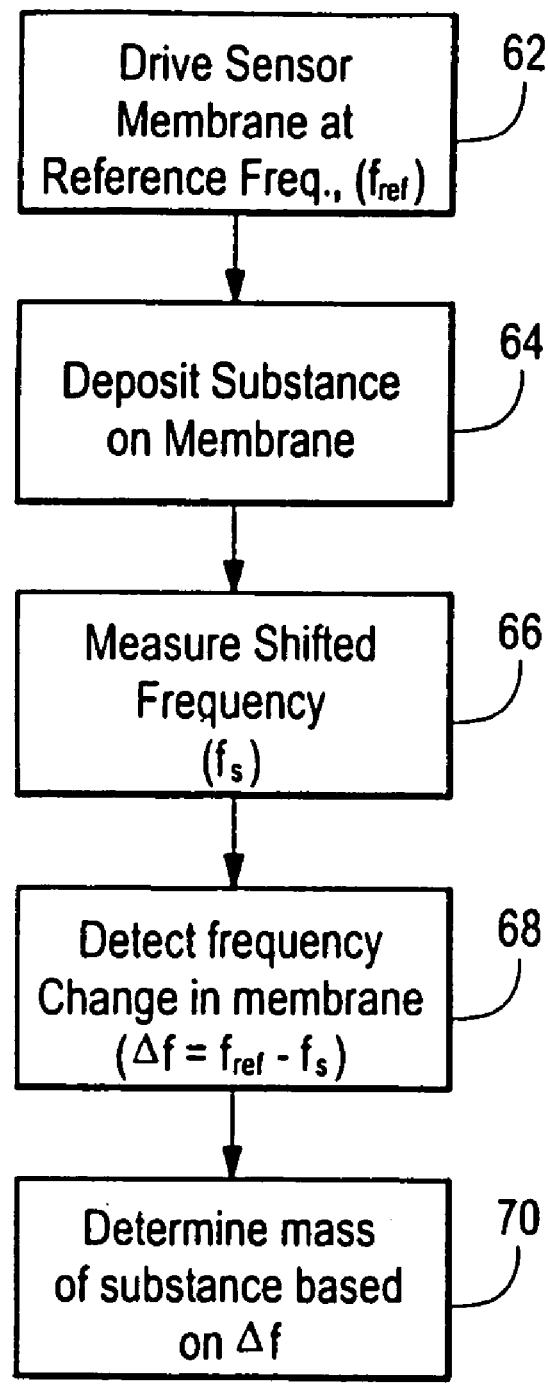
FIG. 6 is a flow chart of the operation of the first embodiment of the present invention.
Figure 7:
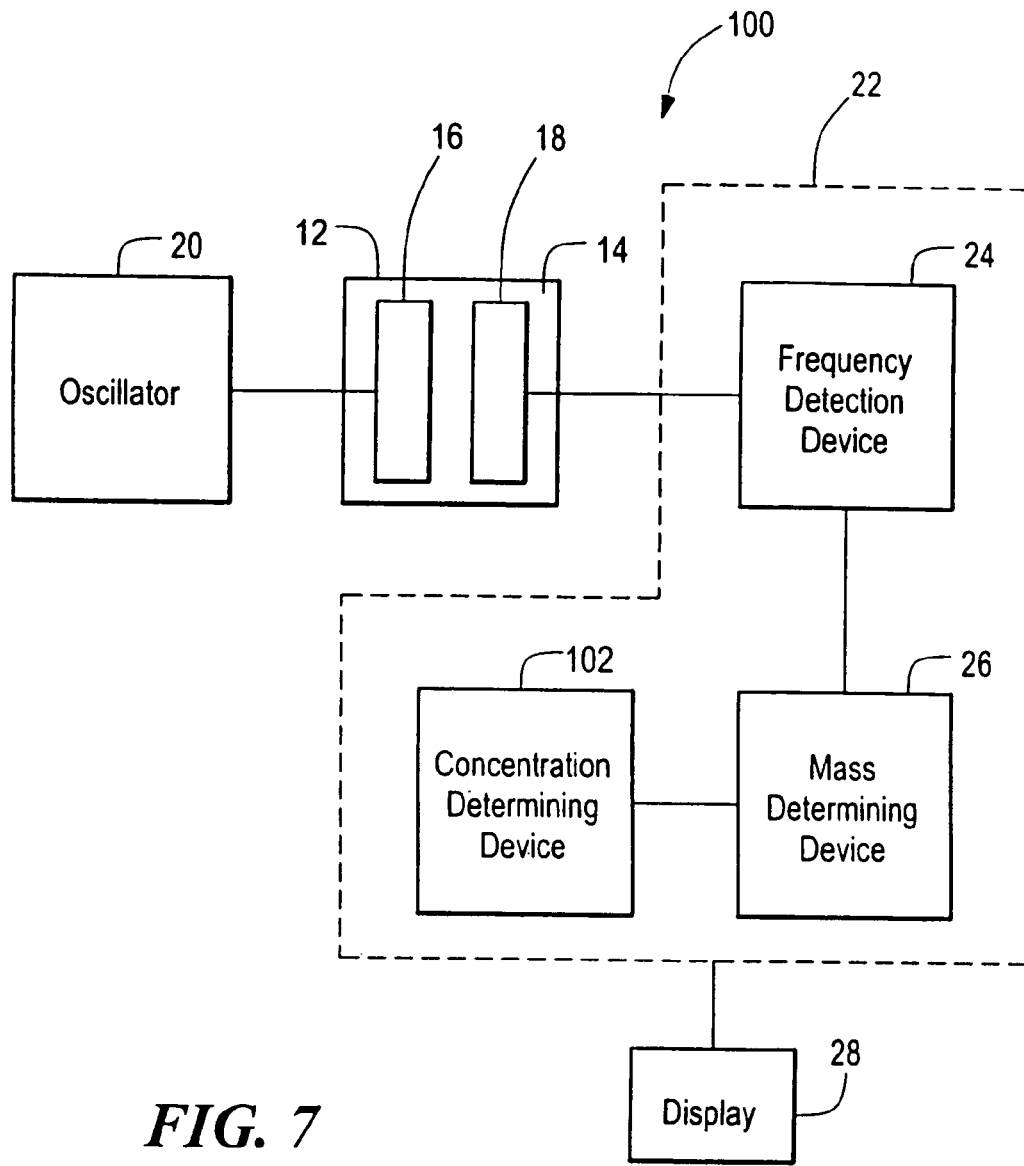
FIG. 7 is a block diagram of a second embodiment of the present invention.
Figure 8:
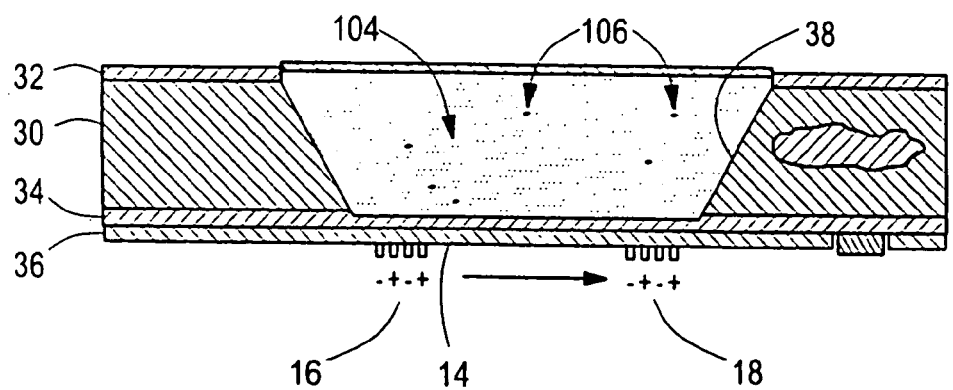
FIG. 8 is a cross-sectional side view of the flexural plate wave sensor of the second embodiment of the present invention taken along line 3—3 of FIG. 2.

A second embodiment of the invention is shown schematically at 100 in FIG. 7. As shown in the figure, the only difference between system 10 of FIG. 1 and system 100 of FIG. 6 is the addition of a concentration determining device 102 within microprocessor 22. In this embodiment, system 100 is used for determining the concentration of a non-volatile residue (NVR) within a volatile solution. As shown in FIG. 8, volatile solution 104, containing NVR 106 is deposited in the cavity 38 of sensor 12 of system 100. Preferably, the volume of the solution 104 is in the range of 1 to 100 microliters. Typically, within minutes, the volatile solution 104 evaporates, leaving the NVR 106 on the membrane 14 of the sensor 12. The mass of the NVR 106 can then be determined and compared to the volume of the solution in concentration determining device 102 to determine the concentration of the NVR within the solution.

Figure 9:
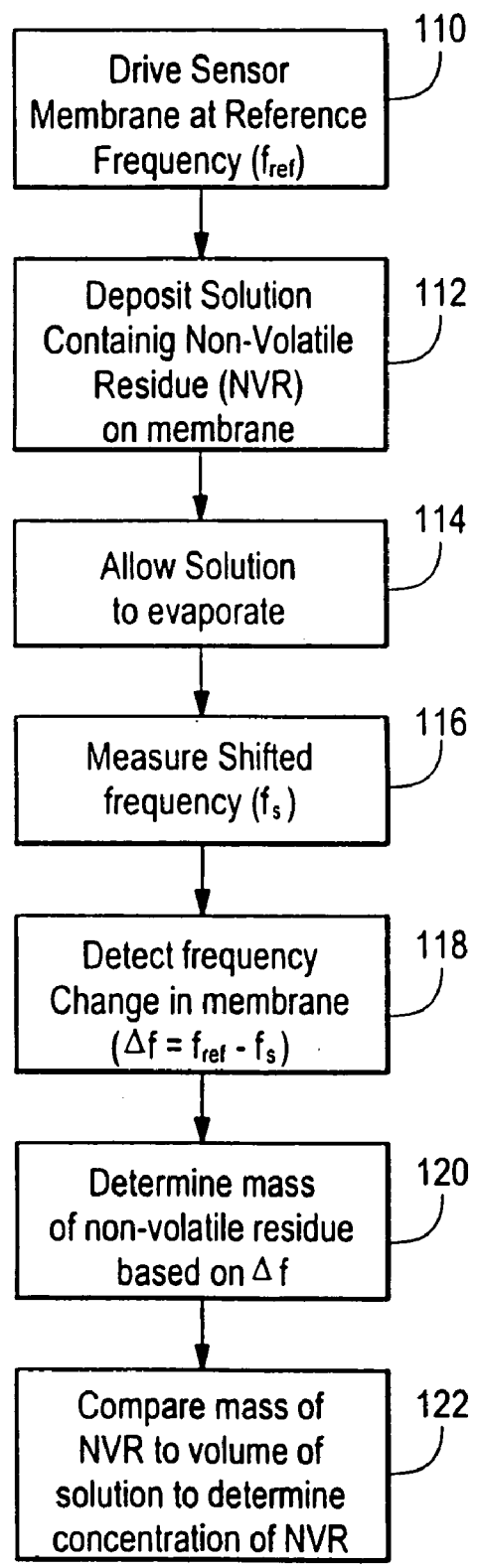
FIG. 9 is a flowchart of the operation of the second embodiment of the present invention.

The operation of the system 100 will now be described with reference to FIG. 9. First, oscillator 20 drives sensor membrane 14 at the reference resonant frequency $f_{ref}$, step 110. The solution 104 containing NVR 106 is then deposited on the membrane 14 within the cavity 38, step 112. After the solution 106 evaporates, step 114, the shifted frequency $f_s$ resulting from the mass of the NVR 106 on the membrane 14 is measured, step 116. The change in frequency between the reference resonant frequency and the shifted frequency, Δf, is then determined by frequency determining device 24, step 118. Mass determining device 26 then determines the mass of the NVR 106 based on the change in frequency, Δf, step 120 and the mass of the NVR 106 is compared to the volume of the solution 104 in concentration determining device 102 to determine the concentration of the NVR 106 in the solution 104. The resulting concentration measurement can then be displayed by optional display 28.

The deposition of the solution 104 on the membrane 14, step 112 in FIG. 6 can be carried out in a number of ways. First, the solution can be directly deposited on the membrane by means of a microliter dropper. Alternatively, the sensor 12 could be placed in an atmosphere in which the solution 104 is present in a fluid or gaseous form, such that the solution will collect on the membrane. For example, in order to test the concentration of paint particles in the atmosphere of an automotive painting facility in which paint is sprayed, the sensor 12 is placed within the facility. As the paint vapor fills the facility, a sample of the vapor will collect on the membrane. The system 100 can then be used to determine the concentration of non-volatile paint particles in the atmosphere of the facility.

Furthermore, the sensor can be used as a passive particle detector. In this case, the sensor is placed in an environment such as a microprocessor fabrication clean room. Since this environment must be sterile for the proper fabrication of the microprocessors, it is important to detect the presence of any foreign particles in the environment. The sensor 12 can be used to detect such particles as they contact the membrane 14 of the sensor 12.

Figure 10:
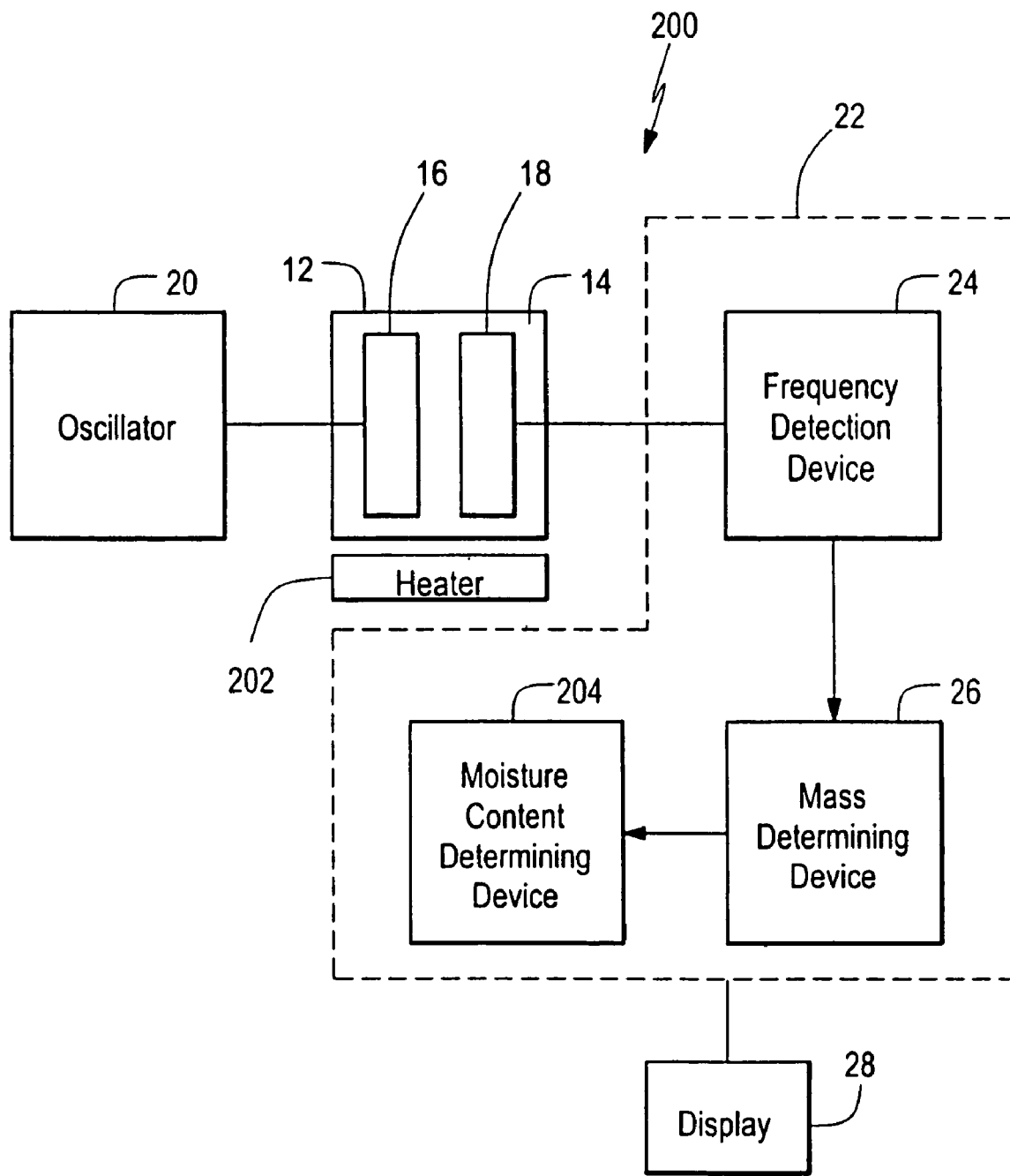
FIG. 10 is a block diagram of third embodiment of the present invention.

A third embodiment of the present invention, shown schematically at 200 in FIG. 10, can be used for thermogravimetric analysis of substances, in order to determine the moisture content of a substance and the boiling point of a substance. System 200, in addition to the elements shown in FIG. 1, includes a heater 202 for heating the sensor 12 for evaporating any moisture in the substance which is placed on membrane 14 of sensor 12 and a moisture content determining device 204 located within microprocessor 22.

Figure 11:
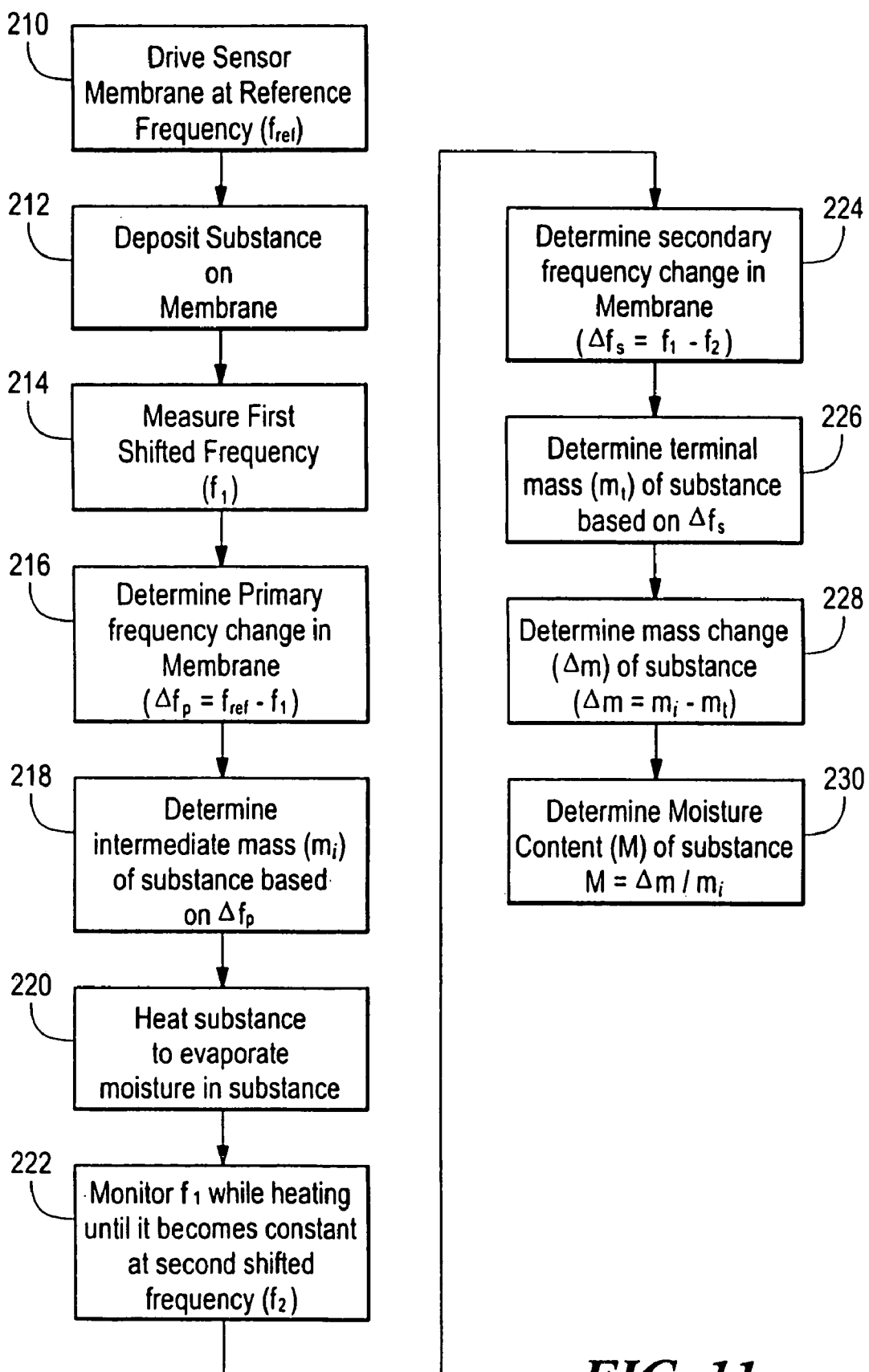
FIG. 11 is a flow chart of the operation of the third embodiment of the present invention.

The operation of the system 200 will now be described with reference to FIG. 11. First, oscillator 20 drives its membrane 14 at the reference resonant frequency, $f_{ref}$, step 210. The substance is deposited on the membrane 14, step 212, and the first shifted frequency, $f_1$, resulting from the increase in mass on the membrane is determined, step 214. The frequency detection device 24 then determines the primary frequency change, $\Delta f_p$, in the membrane 14 by subtracting the first shifted frequency $f_1$ from the reference resonant frequency $f_{ref}$, step 216. Mass determining device 26 then determines the intermediate mass, $m_i$, of the substance based on the primary frequency change $\Delta f_p$, step 218. The substance is then heated using heater 202 to evaporate any moisture in the substance, step 220. While the substance is being heated, frequency detection device 24 monitors the first shifted frequency $f_1$ until it becomes constant at a second shifted frequency $f_2$, step 222 which occurs when all moisture has evaporated from the substance and the mass remains constant. Frequency detection device 24 then determines a secondary frequency change $\Delta f_s$ in the membrane 14 by subtracting the second shifted frequency $f_2$ from the first shift frequency $f_1$, step 224. Mass determining device 26 then determines the terminal mass, $m_t$, of the substance based on the secondary frequency change $\Delta f_s$, step 226. Mass determining device 26 then determines the mass change $\Delta m$ of the substance by subtracting the terminal mass $m_t$ from the intermediate mass $m_i$, step 228, and moisture content determining device 204 determines the moisture content, M, of the substance by dividing the mass change $\Delta m$ by the intermediate mass $m_i$, step 230.

Figure 12:
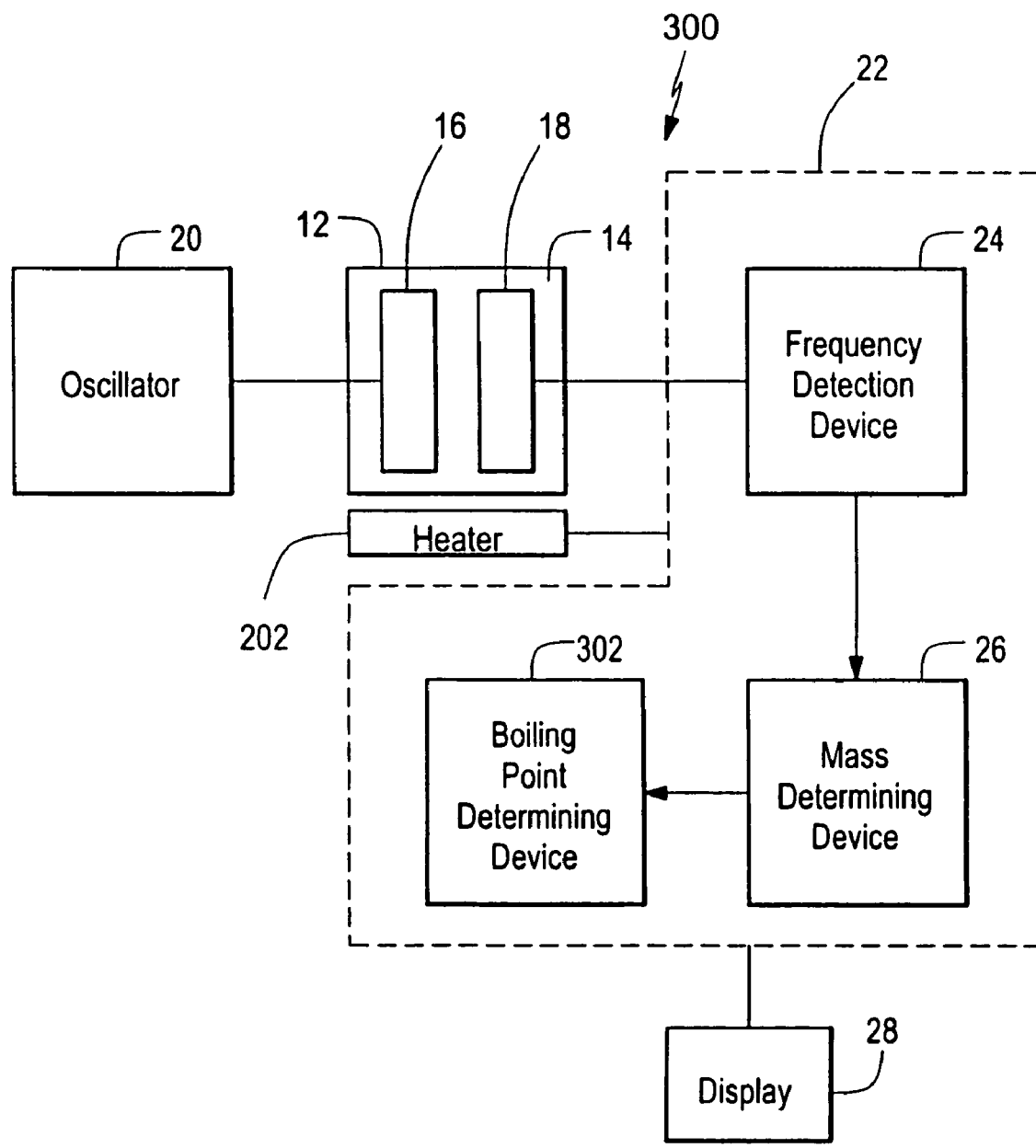
FIG. 12 is a block diagram of the fourth embodiment of the present invention.

Alternatively, the present invention can be used to determine the boiling point of a substance. In this embodiment, shown at 300 in FIG. 12, microprocessor 22 includes a boiling point determining device 302 in addition to the frequency determining device 24 and the mass determining device 26.

Figure 13:
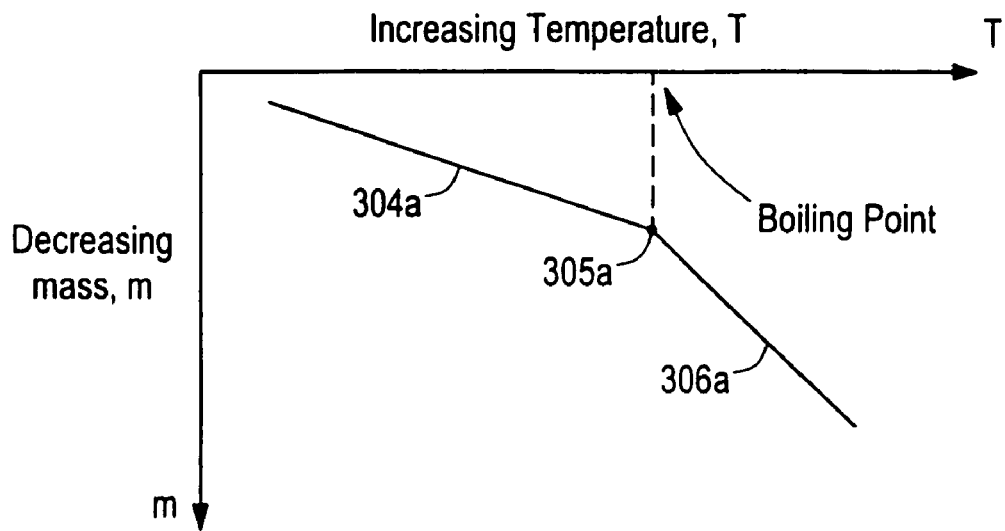
FIG. 13 is a graph that shows the relationship between the mass and temperature of a substance when determining the boiling point of the substance.
Figure 14:
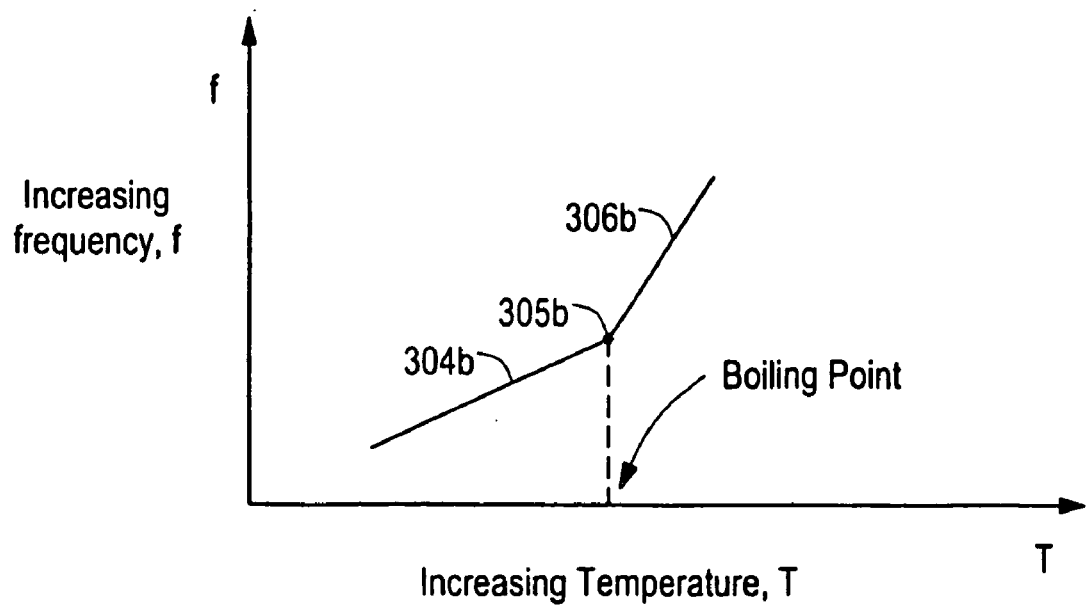
FIG. 14 is a graph that shows the relationship between the frequency of the sensor and the temperature of a substance when determining the boiling point of the substance.

As shown in FIG. 13, as a substance is subjected to a constantly increasing temperature T, the mass of the substance decreases at a steady rate as shown by line 304a until it reaches the boiling point of a substance at point 305a. Once the substance reaches its boiling point, it begins to lose mass at a greater rate, as indicated by line 306a. As discussed above, the rate of change of the mass is inversely proportional to the rate of change of the frequency within the membrane 14. Accordingly, as shown in FIG. 14, as the substance loses mass as it is heated, the frequency within the membrane increases at a steady rate as shown by line 304b until the substance reaches its boiling point at the point 305b. After the substance reaches its boiling point, due to the rapid decrease in the mass of the substance, the frequency within the membrane 14 increases at a greater rate, as indicated by line 306b. In the system 300 of FIG. 12, the rate of change of the frequency within membrane is monitored in order to detect the point where the rate of change of frequency of the membrane 14 changes from the constant shown at line 304b to the constant shown by line 306b, which is greater than the constant shown by line 304b.

Figure 15:
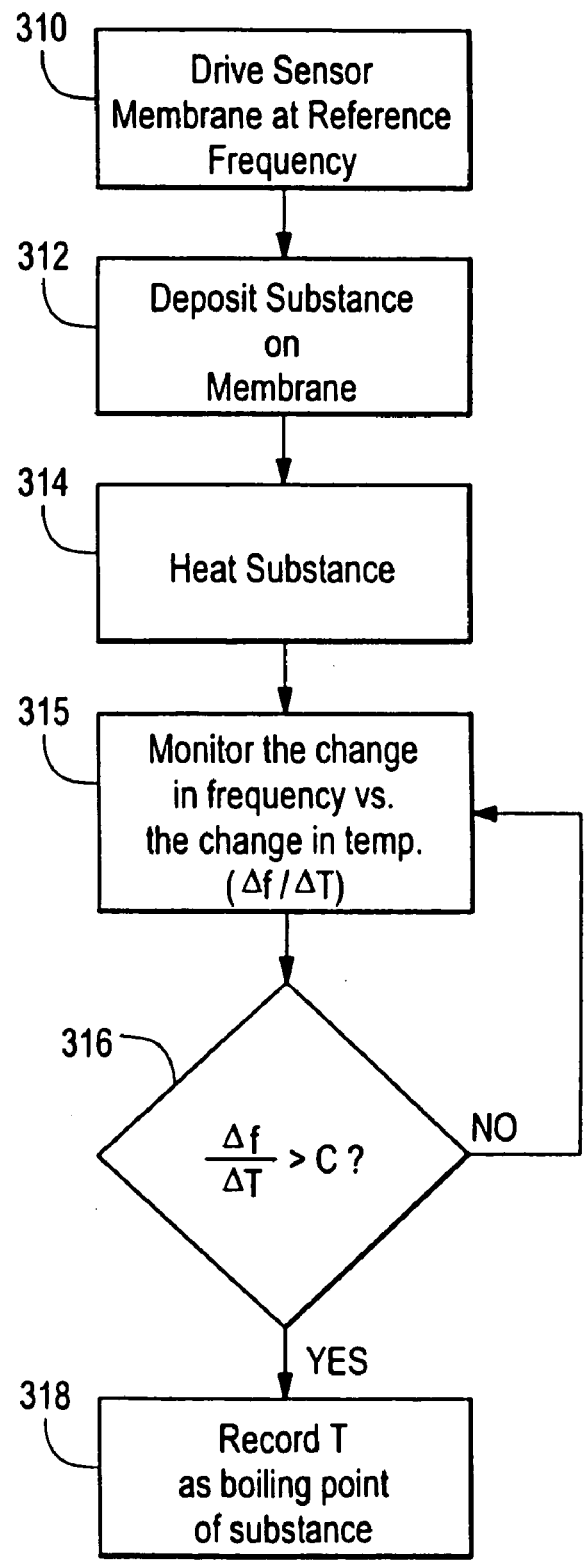
FIG. 15 is a flowchart of the operation of the fourth embodiment of the present invention.

The operation of system 300 will now be discussed with reference to FIG. 15. First, oscillator 20 drives the sensor membrane 14 at a reference resonant frequency, $f_{ref}$, step 310. The substance is deposited on the membrane 14, step 312 and it is heated by heater 202 with a temperature T which is increasing at a known rate $\Delta T$, step 314. As the substance is heated and begins to lose mass, frequency detection device 24 monitors the ratio of the change in the frequency $\Delta f$ in the membrane 14 which is detected by transducer 18 to the change in the temperature $\Delta T$, step 315. If the ratio of $\Delta f$ versus $\Delta T$ ($\Delta f/\Delta T$) is less than or equal to C, which represents the slope of line 304b of FIG. 14, step 316, the boiling point 305b has not yet been reached and the system continues to monitor the ratio of the frequency change to the temperature change, step 315. If the ratio $\Delta f/\Delta T$ is detected as being greater than C, indicating that boiling point 305a, has been reached, and the frequency is now increasing at a faster rate than before the boiling point was reached, step 316. The temperature T is then recorded as the boiling point of the substance, step 318.

Figure 16:
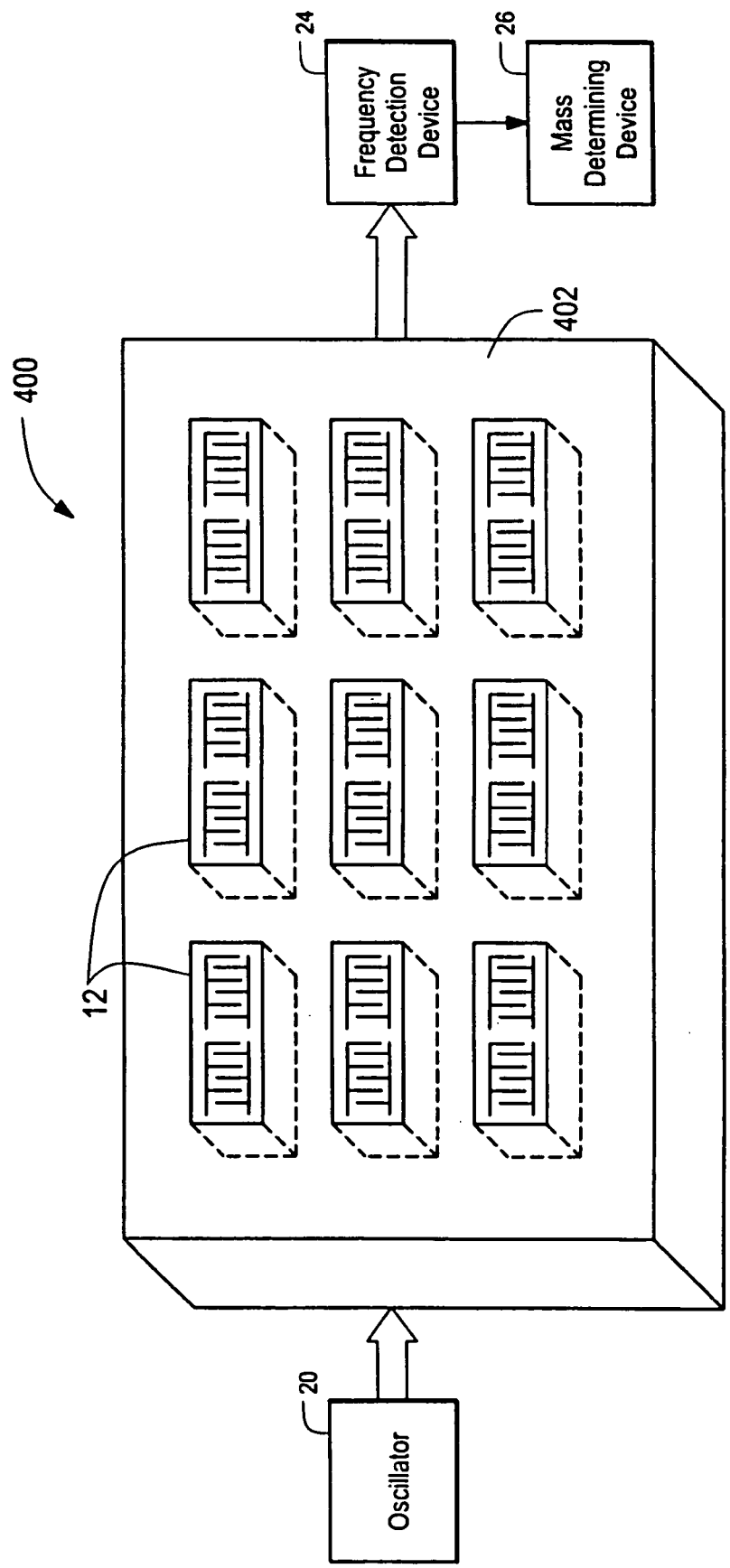
FIG. 16 is a schematic diagram of an array of sensors in accordance with the present invention.

The sensor of the present invention also may be configured in an array as shown at 400 in FIG. 16. Array 400 includes a plurality of sensors 12 disposed on a single chip 402. Each of the sensors 12 is connected between the oscillator 20 which inputs the reference resonant frequency to each of the sensors 12 and the frequency detection device 24 which detects a frequency change in each of the sensors 12. In the case of, for example, the paint facility or clean room environment, the frequency change in each of the sensors 12 can be averaged in order to obtain a more precise measurement of the mass change in the environment detected by the array.

It can therefore be seen that the present invention provides an apparatus for measuring the mass of a substance by monitoring the frequency change in a membrane of a flexural plate wave sensor caused by the change in the mass of the membrane. The mass change is determined based on the amount of the resulting frequency change. The sensitivity of the apparatus is dictated by the ability of the frequency determining device to measure the frequency change in the membrane of the sensor. Accordingly, a frequency determining device that is capable of measuring frequency changes in the single Hertz range would render the apparatus of the present invention capable of measuring mass changes in the subnanogram range.

Although specific features of the invention are shown in some drawings and not in others, this is for convenience only as each feature may be combined with any or all of the other features in accordance with the invention.

Other embodiments will occur to those skilled in the art and are within the following claims:

What is claimed is:

1. An apparatus comprising:
a sensor having a membrane layer, the membrane for receiving the substance thereon;
an oscillator device for driving said membrane at a reference resonant frequency;
a frequency detection device for determining a change in the reference resonant frequency caused by the presence of the substance on the membrane;
a heating device for heating said substance to evaporate moisture from said substance, said frequency detection device determining the change in the reference resonant frequency after the moisture is evaporated from said substance;
a mass determining device for determining the mass of the substance, the amount of change in the reference resonant frequency being indicative of the mass of the substance; and
a moisture content determining device for determining the moisture content of the substance by comparing the mass of the substance before it is heated to the mass of the substance after it is heated.

2. A method comprising:
driving a membrane of a sensor at a reference resonant frequency;
depositing the substance onto the membrane of the sensor;
measuring a shifted frequency within the membrane;
detecting a change of the shifted frequency from the reference resonant frequency;
determining the mass of the substance based on the change of the shifted frequency from the reference resonant frequency;
heating the substance after the mass of the substance is determined to evaporate any moisture in the substance;
measuring the post-heating frequency in the membrane;
detecting a change of the post-heating frequency from the shifted frequency;
determining the mass of the substance based on the change of the post heating frequency from the shifted frequency; and
determining the moisture content of the substance based on the difference in the mass of the substance before the heating step and the mass of the substance after the heating step.

3. A system comprising:
a sensor having a membrane layer for receiving a substance thereon;
an oscillator for driving the membrane layer at a reference resonant frequency;
a solution deposition device for delivering a known quantity of the substance to the membrane layer;
a transducer for detecting the change in frequency of the membrane layer due to the substance;
a heating device for heating the to evaporate any moisture in the substance; and
a processor configured to automatically determine the mass of the particles based on the change in frequency, and to determine the moisture content of the substance based on the difference in the mass of the substance before heating the substance and the mass of the substance after heating the substance.

4. The system of claim 3 wherein said sensor is a flexural plate wave sensor.

5. The system of claim 4 wherein said flexural plate wave sensor is formed from a silicon substrate and said membrane is formed from a silicon layer.

6. The system of claim 4 wherein said flexural plate wave sensor further includes a piezoelectric layer formed on said membrane layer, and said transducer includes a first transducer disposed on said piezoelectric layer and a second transducer disposed on said piezoelectric layer, spaced from said first transducer.

7. The system of claim 6 wherein said oscillator device is connected to said first transducer for driving said membrane at said reference resonant frequency and said processor includes a frequency detection device connected to said second transducer for determining the change in said reference frequency.

8. The system of claim 3 wherein said sensor further includes a plurality of walls peripheral to said membrane, said plurality of walls cooperating to define a cavity having said membrane as a bottom portion thereof.

9. The system of claim 3 wherein the deposition of the substance on the membrane causes a decrease in the reference resonant frequency, thereby indicating an increase in the mass of the substance disposed on the membrane.

10. The system of claim 3, wherein said substance is present in a volume of a volatile solution which is deposited on said membrane, the mass of the substance being measured after the solution evaporates, leaving the substance on the membrane.

11. The system of claim 3 wherein the substance is a non-volatile residue.

12. The system of claim 3 further including a display device connected to said processor for displaying the mass of said substance.

13. The system of claim 3 wherein an increase in the reference resonant frequency indicates a decrease in the mass of the substance on the membrane.

14. The system of claim 3 including a plurality of sensors configured in an array, each of the sensors being connected between said oscillator device and said frequency detection device.

15. The system of claim 3 in which said system measures the mass of a substance when the substance is present at values as low as about 200 picograms/mm$^2$.

* * * * *